US012687552B2

(12) United States Patent
Maeda et al.

(10) Patent No.: US 12,687,552 B2
(45) **Date of Patent: *Jul. 21, 2026**

(54) METHOD FOR SENSING PLANT HORMONE USING RARE EARTH COMPOUND, SENSOR USING THE SAME, AND METHOD FOR EARLY DETECTION OF DISEASE INFECTION IN PLANT

(71) Applicant: NEC CORPORATION, Tokyo (JP)

(72) Inventors: Katsumi Maeda, Tokyo (JP); Shigeyuki Iwasa, Tokyo (JP)

(73) Assignee: NEC CORPORATION, Tokyo (JP)

( * ) Notice: Subject to any disclaimer, the term of this patent is extended or adjusted under 35 U.S.C. 154(b) by 898 days.

This patent is subject to a terminal disclaimer.

(21) Appl. No.: 18/008,076

(22) PCT Filed: Jun. 3, 2021

(86) PCT No.: PCT/JP2021/021169

§ 371 (c)(1),
(2) Date: Dec. 2, 2022

(87) PCT Pub. No.: WO2021/246480

PCT Pub. Date: Dec. 9, 2021

(65) Prior Publication Data

US 2023/0236210 A1 Jul. 27, 2023

(30) Foreign Application Priority Data

Jun. 3, 2020 (JP) ................................ 2020-096909
Mar. 11, 2021 (JP) ................................ 2021-039138

(51) Int. Cl.
*G01N 33/74* (2006.01)
*C09K 11/06* (2006.01)
(Continued)

(52) U.S. Cl.
CPC .............. *G01N 33/74* (2013.01); *C09K 11/06* (2013.01); *G01N 21/6428* (2013.01);
(Continued)

(58) Field of Classification Search
None
See application file for complete search history.

(56) References Cited

U.S. PATENT DOCUMENTS

2018/0142277 A1 5/2018 Ramasamy et al.
2018/0180564 A1 6/2018 Farhart et al.

FOREIGN PATENT DOCUMENTS

JP 3134499 U 8/2007
WO 2011/088540 A1 7/2011
WO 2019/082942 A1 5/2019

OTHER PUBLICATIONS

Satoko Hosokawa, "Communication between plants via odor", J. Japan Association on Odor Environment, 2005, pp. 153-155, vol. 36 No. 3.

(Continued)

*Primary Examiner* — Xiaoyun R Xu
(74) *Attorney, Agent, or Firm* — Sughrue Mion, PLLC

(57) ABSTRACT

Provided is a method for sensing methyl salicylate, which is a plant hormone released when a plant is infected with a disease in cultivation of plants including agricultural crops, and thereby provided a method for early in-situ detection of disease infection in a plant. With the present embodiment, disease infection in a plant can be detected at an early stage by utilizing a rare earth compound that selectively recognizes and forms a complex with methyl salicylate, which is a plant hormone released when a plant is infected by a pathogen, as a receptor for sensing, and by utilizing a (Continued)

(a)

(b)

fluorescence emission phenomenon and a change in electrochemical behavior after the reaction with methyl salicylate.

16 Claims, 9 Drawing Sheets

(51) Int. Cl.
*G01N 21/64* (2006.01)
*G01N 27/327* (2006.01)
*G01N 27/48* (2006.01)
*G01N 33/543* (2006.01)

(52) U.S. Cl.
CPC ......... *G01N 27/3277* (2013.01); *G01N 27/48* (2013.01); *G01N 33/54373* (2013.01); *C09K 2211/1007* (2013.01); *C09K 2211/182* (2013.01); *G01N 2021/6439* (2013.01)

(56) References Cited

OTHER PUBLICATIONS

International Search Report of PCT/JP2021/021169 dated Aug. 31, 2021 [PCT/ISA/210].

(a) (b)

(a) (b)

(a) (b)

(a) (b)

(a) (b)

(a) (b)

METHOD FOR SENSING PLANT HORMONE USING RARE EARTH COMPOUND, SENSOR USING THE SAME, AND METHOD FOR EARLY DETECTION OF DISEASE INFECTION IN PLANT

CROSS REFERENCE TO RELATED APPLICATIONS

This application is a National Stage of International Application No. PCT/JP2021/021169, filed Jun. 3, 2021, claiming priority to Japanese Patent Application No. 2020-096909, filed Jun. 3, 2020 and Japanese Patent Application No. 2021-039138, filed Mar. 11, 2021.

TECHNICAL FIELD

The present invention relates to a method for sensing a plant hormone released when a plant is infected with a disease, and a method for early detection of disease infection in a plant.

BACKGROUND ART

It is known that plants have their own defense mechanisms that work against infection by pathogens such as filamentous fungi, feeding damage by insect pests and others, and stress due to environmental changes. Specifically, when plants are infected by pathogens, they synthesize salicylic acid, a signal substance, at the site of infection. Then, salicylic acid moves through the plant body via the sieve tube tissue and induces defense mechanisms in uninfected tissues, resulting in the development of systemic resistance to pathogens (systemic acquired resistance). Also, when plants undergo feeding damage by insect pests, they synthesize ethylene and jasmonic acid, which, in the same manner as salicylic acid, move through the plant body and induce defense mechanisms systemically (induced systemic resistance). Furthermore, it is known that plants adapt to environmental stress by synthesizing abscisic acid in the plant body in response to changes in the growth environment, such as drought, low temperature, and salt damage.

It is also known that, when plants are infected by pathogens or undergo feeding damage by insect pests, they have a mechanism to inform not only the damaged plants themselves but also the surrounding plants (Non-Patent Document 1). Specifically, salicylic acid, which is synthesized when infected by pathogens, is methylated to be methyl salicylate, which is released from the plants as a volatile signal substance to inform the surrounding plants of the pathogen infection, thus promoting defense mechanisms in advance. Jasmonic acid, which is synthesized at the time of damage by insect pests, is also known to be methylated to be methyl jasmonate, which is a volatile signal released from the plants, inducing resistance in the surrounding plants in advance.

As described above, it is known that plants release plant hormones as signal substances when they are damaged by diseases and insect pests, and sensing such signal substances as quickly as possible makes possible early detection of damage by diseases and insect pests.

As the method for early discovery of damage by sensing jasmonic acid released as a volatile signal at the time of insect pest damage, a method is disclosed in which a monitor plant with a luminescent protein gene is cultivated alongside a cultivated crop, and a phenomenon is utilized in which the monitor plant senses methyl jasmonate released and emits light when the crop undergoes damage by insect pests (Patent Document 1).

CITATION LIST

Patent Document

Patent Document 1: International Publication No. WO2019/082942

Non-patent Document

Non-Patent Document 1: J. Japan Association on Odor Environment, Vol. 36, No. 3, 153-155(2005).

SUMMARY OF INVENTION

Technical Problem

An object of the present invention is to provide a method for sensing methyl salicylate, which is a plant hormone released when a plant is infected with a disease, in the cultivation of plants including crops, as well as such a sensor, thereby providing a method for early in-situ detection of disease infection in a plant.

Solution to Problem

The present invention utilizes a rare earth compound that selectively recognizes and forms a complex with methyl salicylate, which is a volatile plant hormone, as a receptor for sensor. Also, the present invention detects disease infection in a plant at an early stage by utilizing a fluorescence emission phenomenon of a complex produced by a reaction of methyl salicylate and a rare earth compound. Furthermore, the present invention detects disease infection in a plant at an early stage by utilizing a phenomenon in which electrochemical behavior is changed by a reaction of methyl salicylate and a rare earth compound.

Advantageous Effect of Invention

By using a rare earth compound of the present invention as a receptor for a sensor, methyl salicylate, a volatile plant hormone released when a plant is infected by a pathogen, can be selectively sensed, and furthermore, infection in a plant by a pathogen can be detected at an early stage by utilizing a fluorescence emission phenomenon from a complex formed by a reaction of methyl salicylate and the rare earth compound, or by utilizing a change in electrochemical behavior.

BRIEF DESCRIPTION OF DRAWINGS

FIG. 17 shows a photograph confirming fluorescence emission obtained in Example 12.

DESCRIPTION OF EMBODIMENTS

Figure 1:
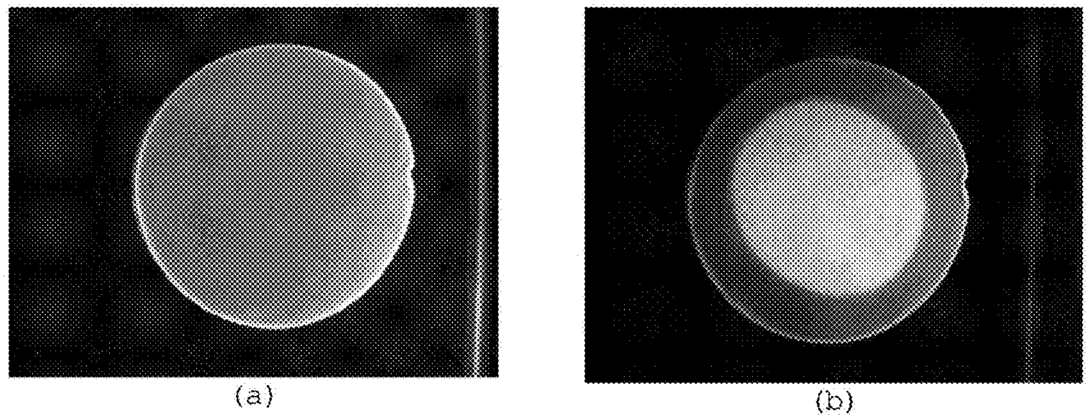
FIG. 1 shows photographs for confirming fluorescence emission in Example 1.

Hereinafter, embodiments of the present invention will be described with reference to the accompanying drawings and others. However, while the embodiments mentioned below have technically preferred limitations for implementing the present invention, they are not intended to limit the scope of the invention to those described below.

The present inventors have conducted diligent studies in order to solve the above-mentioned problem. As a result, they have found that methyl salicylate, which is a volatile signal substance released when a plant is infected by a pathogen, can be selectively sensed by using a rare earth compound, thus completing the present invention.

Hereinafter, the present embodiments will be described in detail.

<Receptor for Methyl Salicylate: Rare Earth Compound>

Examples of the rare earth compound that may be used as a receptor for sensing methyl salicylate include a salt of a rare earth element, including a salt of scandium (Sc), yttrium (Y), lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), or lutetium (Lu), which belong to rare earth elements; specifically including an acetate, a chloride, an oxalate, a nitrate, a propionate, an isobutyrate, a pivalate of the rare earth element. Specifically, examples thereof include, but are not limited to, scandium acetate hydrate, yttrium acetate tetrahydrate, lanthanum acetate hydrate, cerium acetate monohydrate, praseodymium acetate monohydrate, neodymium acetate monohydrate, samarium acetate hydrate, europium acetate hydrate, gadolinium acetate tetrahydrate, terbium acetate tetrahydrate, dysprosium acetate tetrahydrate, holmium acetate tetrahydrate, erbium acetate tetrahydrate, thulium acetate tetrahydrate, ytterbium acetate tetrahydrate, lutetium acetate tetrahydrate, europium chloride hexahydrate, terbium chloride hexahydrate, dysprosium chloride hexahydrate, terbium nitrate hexahydrate, terbium oxalate decahydrate, terbium propionate, terbium isobutyrate, terbium pivalate, and the like.

For example, terbium acetate can selectively recognize methyl salicylate by forming a complex with methyl salicylate by the reaction shown in Formula (1) below.

Formula (1)

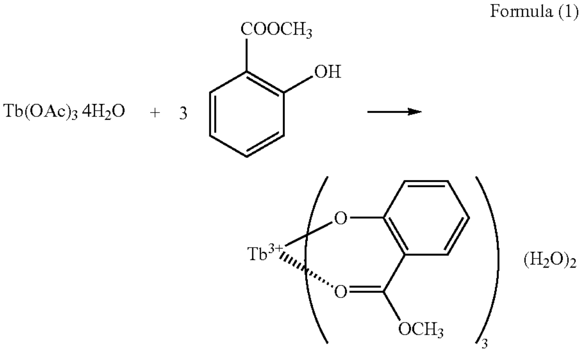

A complex compound formed by a salt of a rare earth element and a phosphine oxide derivative may be also used. Examples of the phosphine oxide derivative include, but are not limited to, triphenylphosphine oxide, tributylphosphine oxide, trihexylphosphine oxide, tricyclohexylphosphine oxide, tris(4-methoxyphenyl) phosphine oxide, 4-(dimethylamino)phenyl diphenyl phosphine oxide, tri(2-thienyl) phosphine oxide, 1,3-bis(diphenylphosphino)propanedioxide, 1,4-bis(diphenylphosphino)butanedioxide, bis[2-(diphenylphosphino)phenyl]ether dioxide, 4,5-bis (diphenylphosphino)-9,9-dimethylxanthene dioxide, and the like.

The phosphine oxide derivative of a salt of a rare earth element is synthesized by heat reaction of the salt of rare earth element and the phosphine oxide in methanol.

For example, a complex of terbium acetate and triphenylphosphine oxide is synthesized by heating to reflux terbium acetate and triphenylphosphine oxide in methanol for 4 hours as shown in Formula (2) below.

Formula (2)

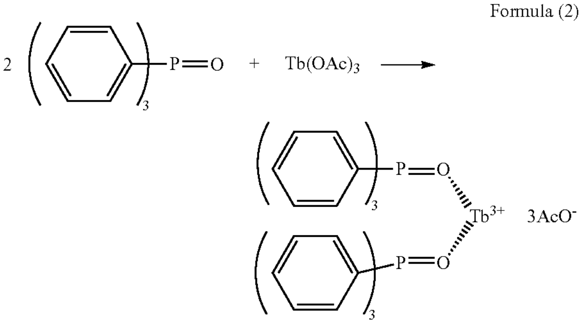

The complex of terbium acetate and phosphine oxide can selectively recognize methyl salicylate by forming a complex with methyl salicylate through the reaction shown in Formula (3) below.

Formula (3)

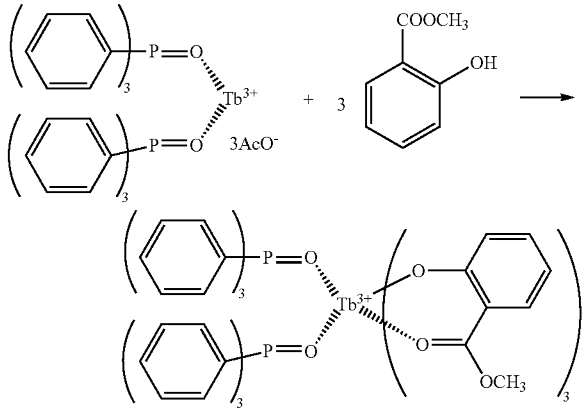

Thus, some embodiments of the present invention relate to a method for detecting methyl salicylate, comprising a step of reacting a rare earth compound and methyl salicylate to form a complex.

Some embodiments of the present invention relate to a sensing method for sensing methyl salicylate, using a rare earth compound as a receptor that selectively recognizes methyl salicylate.

In some embodiments, terbium (III) acetate tetrahydrate may be used as the rare earth compound. In some embodiments, dysprosium (III) acetate tetrahydrate is used as the rare earth compound. In some embodiments, gadolinium (III) acetate tetrahydrate is used as the rare earth compound.

In some embodiments, the reaction of the rare earth compound and methyl salicylate is carried out in a solution. The solution may be, but is not limited to, a dimethyl sulfoxide solution, a methanol solution, or an aqueous solution. In some embodiments, the concentration of the rare earth compound may be, for example, in the range of 0.00001 mol/L to 5 mol/L, such as in the range of 0.00004 mol/L to 1 mol/L.

In some embodiments, the reaction of the rare earth compound and methyl salicylate is carried out in a solid medium. The solid medium may be, but is not limited to, paper or glass (for example, a glass fiber, a porous glass substrate), or resin (for example, polymethyl methacrylate, polyethylene, polypropylene, polyvinyl chloride, polystyrene, nylon resin, polyamide, polycarbonate, polyethylene terephthalate, polybutylene terephthalate, polyphenylene oxide) or water-soluble polymer (such as cellulose-based polymer, agarose, starch-based polymer, sodium arginate, acrylate-based polymer, acrylamide-based polymer, polyvinyl alcohol, polyethylene oxide, polyvinylpyrrolidone).

<Fluorescence Emission Phenomenon>

The complex produced by the reaction of the rare earth compound and methyl salicylate newly exhibits fluorescence emission. Specifically, the complex formed by the reaction of the rare earth compound and methyl salicylate exhibits fluorescence emission by exposing it to excitation light with a wavelength of 200 to 400 nm. On the other hand, the rare earth compound alone little fluorescence emission, which makes it possible to detect methyl salicylate.

Thus, some embodiments of the present invention relate to a method for detecting methyl salicylate, comprising: (i) a step of allowing a rare earth compound to react with methyl salicylate to form a complex; (ii) a step of exposing the complex to excitation light; and (iii) a step of detecting fluorescence emitted by the complex. In some embodiments, an appropriate wavelength in the range of 200 to 400 nm is selected as the excitation wavelength. Furthermore, in some embodiments, a step of comparing the intensity of the detected fluorescence with a predetermined reference value to determine the concentration of methyl salicylate may also be performed.

Some embodiments of the present invention relate to a method for sensing methyl salicylate, utilizing a phenomenon in which methyl salicylate reacts with the rare earth compound to form a rare earth complex, resulting in fluorescence emission.

<Electrochemical Behavior>

The complex produced by the reaction of the rare earth compound and methyl salicylate exhibits electrochemical behavior that is different from that of the receptor, the rare earth compound. Specifically, a cyclic voltammetry measurement of an electrochemical cell containing the complex formed by the rare earth compound and methyl salicylate shows that a large change in current value occurs around a certain potential. This makes it possible to detect methyl salicylate by monitoring this current value.

Some embodiments of the present invention relate to a method for detecting methyl salicylate, comprising: (i) a step of allowing a rare earth compound to react with methyl salicylate in a solution to form a complex; (ii) a step of measuring a current flowing under a certain voltage; and (iii) a step of detecting a change in current value caused by formation of the complex. In some embodiments, an appropriate value in the range of −1 to 2 V (vs. Normal Hydrogen Electrode (NHE), is selected as a value of the voltage. The solution may contain tetrabutylammonium perchlorate as a supporting electrolyte, for example, but the supporting electrolyte is not limited to this. In some embodiments, a step of comparing the detected change in current value with a predetermined reference value to determine the concentration of methyl salicylate may also be performed.

Some embodiments of the present invention relate to a method for sensing methyl salicylate, utilizing a phenomenon in which a rare earth compound reacts with methyl salicylate to form a complex, and the electrochemical behavior of the complex is different from that of the rare earth compound.

Some embodiments of the present invention relate to a method for sensing methyl salicylate, utilizing a phenomenon in which a rare earth compound reacts with methyl salicylate to form a complex and the current value of the complex in a certain potential region is different from that of the rare earth compound.

In some embodiments, the method for sensing methyl salicylate of the present invention may be used for detecting pathogen infection in a crop.

<Methyl Salicylate Sensor>

A methyl salicylate sensor of the present invention using a rare earth compound as a receptor comprises at least a recognition section for methyl salicylate and a detection section that detects recognition of methyl salicylate by the recognition section. The recognition section at least comprises a rare earth compound, which is a receptor. The rare earth compound does not react with or recognize other plant hormones other than methyl salicylate, such as methyl jasmonate, and can therefore selectively recognize methyl salicylate. The detection section is configured to be able to optically and/or electrochemically detect recognition of methyl salicylate by the recognition section for methyl salicylate. For example, the optical detection section comprises at least an excitation light source and a detection element in order to detect fluorescence emission of a complex produced by the rare earth compound and methyl salicylate, and detects methyl salicylate and measures the concentration thereof based on a change in fluorescence intensity. In order to detect a change in electrochemical behavior, for example, the electrochemical detection section constructs an electrochemical cell (detection element) with an electrode to detect a current caused by redox reaction of a complex formed by the reaction of the rare earth compound and methyl salicylate, and detects methyl salicylate and measures the concentration thereof using a change in electrochemical behavior of the electrochemical cell (for example, change in current value at a certain potential).

Thus, some embodiments of the present invention relate to a methyl salicylate sensor for detecting methyl salicylate, at least comprising: a recognition section for methyl salicylate that comprises a rare earth compound, which is a receptor that selectively recognizes methyl salicylate; and a detection section that detects recognition of methyl salicylate by the recognition section. In some embodiments, the methyl salicylate sensor of the present invention detects methyl salicylate, which is a plant hormone released when a crop is infected by a pathogen. Thus, the methyl salicylate sensor of the present invention may be used as a sensor for detecting pathogen infection in a crop. In some embodiments, the methyl salicylate sensor of the present invention can selectively detect methyl salicylate compared to methyl jasmonate.

Some embodiments of the present invention relate to a methyl salicylate sensor for detecting methyl salicylate, at least comprising: (i) a recognition section for methyl salicylate that comprises a rare earth compound; and (ii) a detection section that optically detects recognition of methyl salicylate by the recognition section. In some embodiments, the optical detection section at least comprises an excitation light source and a detection element. In some embodiments, the methyl salicylate sensor of the present invention can detect methyl salicylate and/or measure the concentration thereof based on a change in the observed fluorescence intensity.

Some embodiments of the present invention relate to a methyl salicylate sensor for detecting methyl salicylate, at least comprising: (i) a recognition section for methyl salicylate that comprises a rare earth compound; and (ii) a detection section that electrochemically detects recognition of methyl salicylate by the recognition section. In some embodiments, the electrochemical detection section comprises an electrochemical cell having an electrode that detects a current caused by redox reaction of a complex formed by the rare earth compound and methyl salicylate. In some embodiments, the methyl salicylate sensor of the present invention can detect methyl salicylate and/or measure the concentration thereof based on a change in current value of the electrochemical cell.

In some embodiments, the detection section may comprise a computer that executes a program to process detection of methyl salicylate and/or measurement of the concentration thereof. Such a program may be, for example, a program that causes the computer to execute a step of receiving a signal from the optical and/or electrochemical detection element, a step of analyzing the received signal to determine the presence or absence of methyl salicylate and/or the concentration thereof, and a step of outputting the analysis result. In some embodiments, the analysis of the received signal may include comparing the received signal with a predetermined reference value to determine the presence or absence of methyl salicylate and/or the concentration thereof, for example. In some embodiments, the analysis result may be output to, for example, a display device connected to the sensor, or other equipment or the like connected via a network.

Thus, some embodiments of the present invention relate to a methyl salicylate sensor for detecting methyl salicylate, the methyl salicylate sensor at least comprising: a recognition section for methyl salicylate that comprises a rare earth compound, which is a receptor that selectively recognizes methyl salicylate; and a detection section that detects recognition of methyl salicylate by the recognition section, the detection section comprising a detection element and a computer, wherein the program causes the computer to execute: (i) a step of receiving a signal from the optical and/or electrochemical detection element; (ii) a step of analyzing the received signal to determine the presence or absence of methyl salicylate and/or the concentration thereof; and (iii) a step of outputting the analysis result.

<Method for Early Detection of Pathogen Infection in Crop>

As one application of the methyl salicylate sensor of the present invention, by installing the methyl salicylate sensor near where a crop is planted and detecting methyl salicylate by the sensor, it is possible to detect pathogen infection in the crop at an early stage.

Thus, some embodiments of the present invention relate to a method for detecting pathogen infection in a crop, comprising installing a methyl salicylate sensor in the vicinity of the crop, and detecting methyl salicylate by the sensor. In some embodiments, the methyl salicylate sensor is a methyl salicylate sensor at least comprising: a recognition section for methyl salicylate that comprises a rare earth compound, which is a receptor that selectively recognizes methyl salicylate; and a detection section that detects recognition of methyl salicylate by the recognition section. In some embodiments, the methyl salicylate sensor is a methyl salicylate sensor at least comprising: (i) a recognition section for methyl salicylate that comprises a rare earth compound; and (ii) a detection section that optically and/or electrochemically detects recognition of methyl salicylate by the recognition section.

Examples of the crop that may be the monitoring target include, but are not limited to, cucumber, watermelon, tomato, eggplant, green pepper, paprika, shishito pepper, melon, Chinese cabbage, cabbage, radish, lettuce, leek, broccoli, onion, garlic, Japanese yam, asparagus, carrot, potato, celery, tobacco, rice, and strawberry.

Examples of the disease that may be detected include, but are not limited to, ring spot disease, leaf spot, Corynespora target spot, leaf mold, fusarium wilt, root rot wilt, Verticillium wilt, brown root rot, gray phytophthora rot, root rot, black dot root rot, southern blight, damping off, brown leaf spot, downy mildew, powdery mildew, gray mold, anthracnose, scab, Sclerotinia rot, gummy stem blight, leaf spot, blight, mosaic disease, spotted wilt, yellow leaf curl, bacterial wilt, bacterial soft rot, bacterial canker, pith necrosis, bacterial black spot, and bacterial leaf spot, and examples of the pathogen infection that may be detected include, but are not limited to, infections caused by the causative microorganisms of the above diseases.

In the context of the present disclosure, when referring to installing the sensor in the vicinity of the crop, examples of the term “vicinity” include, but are not limited to, a distance within 2 m, within 1 m, within 75 cm, within 50 cm, within 40 cm, within 30 cm, within 20 cm, within 10 cm, or within 5 cm of the crop to be monitored, and an appropriate distance is selected as appropriate in consideration of a variety of factors. A person skilled in the art would be able to set the position of the sensor to be installed as appropriate in consideration of a variety of conditions.

Some embodiments of the present invention relate to the use of a methyl salicylate sensor in detection of pathogen infection in a crop. Some embodiments of the present invention relate to use of a rare earth compound in production of a methyl salicylate sensor.

EXAMPLES

Hereinafter, an embodiment of the present invention will be explained in details by using examples, but the present invention is not limited to these examples.

Example 1

0.2 ml of a solution obtained by dissolving 0.05 g of terbium (III) acetate tetrahydrate (TbA) in 2 ml of water was dropped on a circular filter paper (45 mmΦ) and dried to obtain a filter paper containing TbA. The obtained filter paper was excited with a UV lamp (wavelength 365 nm) to confirm whether fluorescence emission was present (FIG. 1(*a*)). Next, 0.03 ml of an acetonitrile solution (0.1 mol/L) of methyl salicylate (MSA), which is released when a plant is infected by a pathogen, was dropped on that filter paper and dried, and the obtained filter paper was similarly excited with a UV lamp to confirm whether fluorescence emission was present (FIG. 1(*b*)). As a result, it was found that TbA alone does not exhibit fluorescence, but TbA reacts with methyl salicylate and exhibits fluorescence emission, indicating that methyl salicylate can be sensed.

Comparative Example 1

Figure 2:
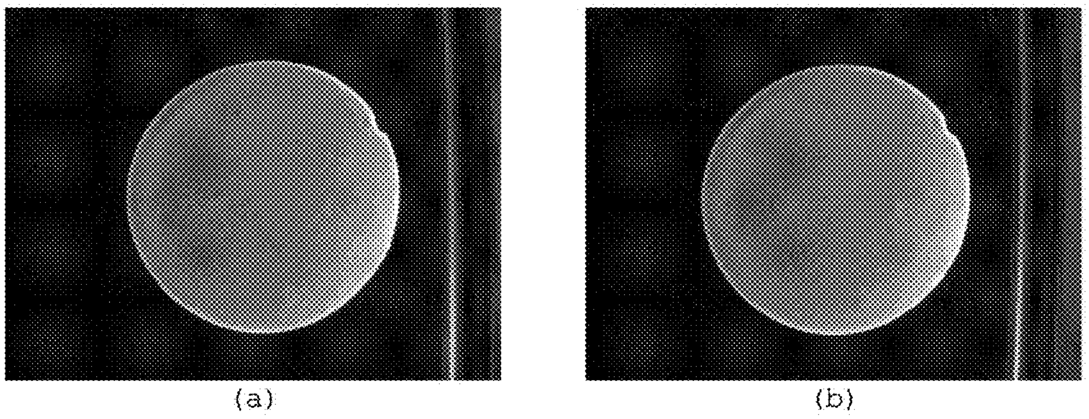
FIG. 2 shows photographs for confirming fluorescence emission in Comparative Example 1.

0.2 ml of a solution obtained by dissolving 0.05 g of terbium (III) acetate tetrahydrate (TbA) in 2 ml of water was dropped on a circular filter paper (45 mmΦ) and dried to obtain a filter paper containing TbA. The obtained filter paper was excited with a UV lamp (wavelength 365 nm) to confirm whether fluorescence emission was present (FIG. 2(*a*)). Next, 0.03 ml of an acetonitrile solution (0.1 mol/L) of methyl jasmonate, which is a signal substance released when a plant undergoes damage by an insect pest, was dropped on that filter paper and dried, and the obtained filter paper was similarly excited with a UV lamp to confirm whether fluorescence emission was present (FIG. 2(*b*)). As a result, it was found that TbA does not react with methyl jasmonate and not exhibit fluorescence emission.

From the results of Example 1 and Comparative Example 1, it was found that TbA can selectively sense methyl salicylate, which is released by a plant at the time of pathogen infection.

Example 2

Figure 3:
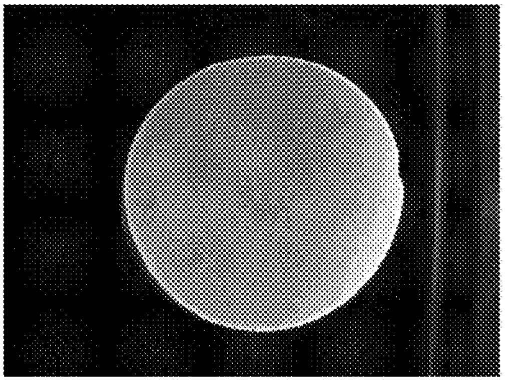
FIG. 3 shows a photograph for confirming fluorescence emission in Example 2.

0.2 ml of a solution obtained by dissolving 0.05 g of terbium (III) acetate tetrahydrate (TbA) in 2 ml of water was dropped on a circular filter paper (45 mind)) and dried to obtain a filter paper containing TbA. Next, this filter paper and 0.05 g of methyl salicylate placed in a Petri dish were left at rest and stored in a desiccator so that they are not in direct contact. After 1 hour, the filter paper was taken out, and the filter paper was excited with a UV lamp (wavelength 365 nm) to evaluate whether fluorescence emission was present, which confirmed yellow-green fluorescence (FIG. 3). From this result, it was found that methyl salicylate, which is released by a plant at the time of pathogen infection, can be sensed as a volatile signal.

Example 3

Figure 4:
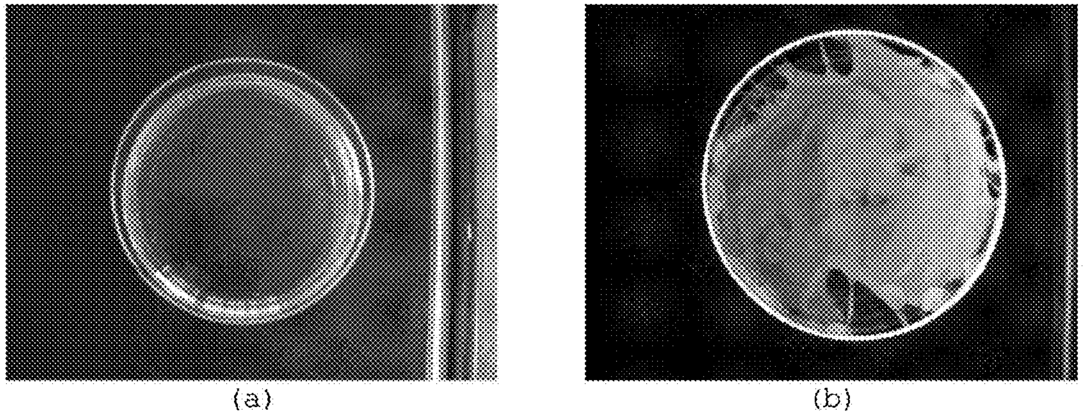
FIG. 4 shows photographs for confirming fluorescence emission in Example 3.

0.1 g of terbium (III) acetate tetrahydrate (TbA) and 0.1 g of polymethyl methacrylate (PMMA) were dissolved in 2 ml of dimethyl sulfoxide. The obtained solution was then spin-coated onto a circular glass substrate (30 mm D) and subsequently dried on a hot plate at 90° C. for 5 minutes to obtain a film coated with PMMA containing TbA. The resulting glass substrate was excited with a UV lamp (wavelength 365 nm) to confirm whether fluorescence emission was present, and no fluorescence was observed (FIG. 4(*a*)). Next, the glass substrate and 0.05 g of methyl salicylate were placed in a petri dish and stored in a desiccator so that they are not in direct contact. After 21 hours, the glass substrate was taken out and excited with a UV lamp (wavelength: 365 nm) to evaluate whether fluorescence emission was present, which confirmed yellow-green fluorescence (FIG. 4(*b*)). From this result, it was found that TbA can sense methyl salicylate, which is released by a plant at the time of pathogen infection as a volatile signal.

Example 4

Figure 5:
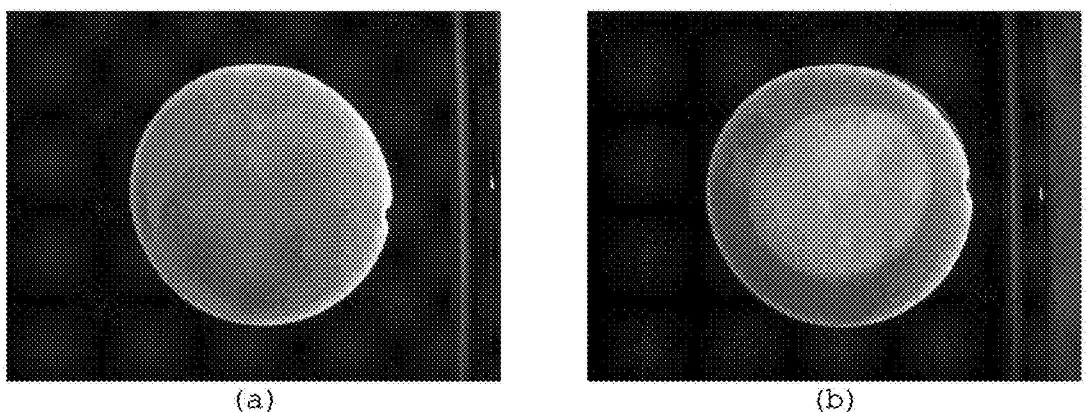
FIG. 5 shows photographs for confirming fluorescence emission in Example 4.

0.2 ml of a solution obtained by dissolving 0.2 g of gadolinium (III) acetate tetrahydrate (GdA) in 2 ml of water was dropped on a circular filter paper (45 mmΦ) and dried to obtain a filter paper containing GdA. The obtained filter paper was excited with a UV lamp (wavelength 365 nm) to confirm whether fluorescence emission was present (FIG. 5(*a*)). Next, 0.03 ml of an acetonitrile solution (0.1 mol/L) of methyl salicylate (MSA), which is released when a plant is infected by a pathogen, was dropped on that filter paper and dried, and the obtained filter paper was similarly excited with a UV lamp to confirm whether fluorescence emission was present (FIG. 5(*b*)). As a result, it was found that GdA alone does not exhibit fluorescence, but GdA reacts with methyl salicylate and exhibits fluorescence emission, indicating that methyl salicylate can be sensed.

Comparative Example 2

Figure 6:
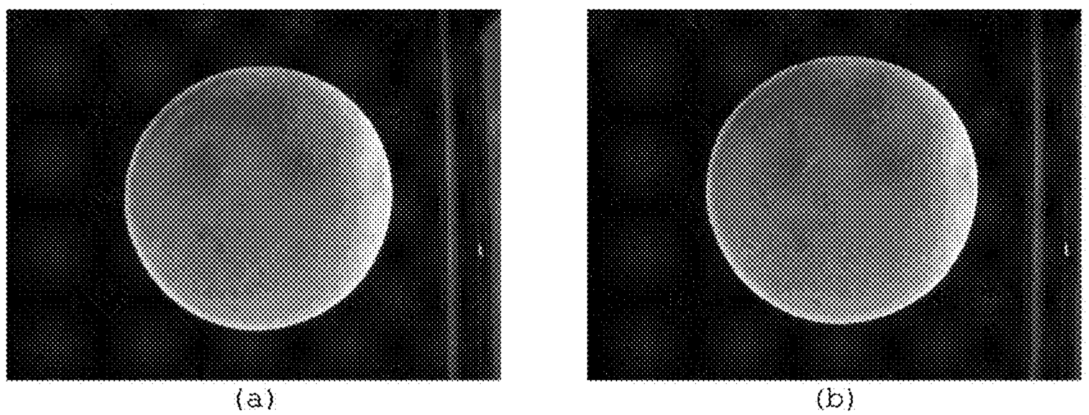
FIG. 6 shows photographs for confirming fluorescence emission in Comparative Example 2.

0.2 ml of a solution obtained by dissolving 0.2 g of gadolinium (III) acetate tetrahydrate (GdA) in 2 ml of water was dropped on a circular filter paper (45 mmΦ) and dried to obtain a filter paper containing GdA. The obtained filter paper was excited with a UV lamp (wavelength 365 nm) to confirm whether fluorescence emission was present (FIG. 6(*a*)). Next, 0.03 ml of an acetonitrile solution (0.1 mol/L) of methyl jasmonate, which is a signal substance released when a plant undergoes damage by an insect pest, was dropped on that filter paper and dried, and the obtained filter paper was similarly excited with a UV lamp to confirm whether fluorescence emission was present (FIG. 6(*b*)). As a result, it was found that GdA does not react with methyl jasmonate and not exhibit fluorescence emission.

From the results of Example 4 and Comparative Example 2, it was found that GdA can selectively sense methyl salicylate, which is released by a plant at the time of pathogen infection.

Example 5

Figure 7:
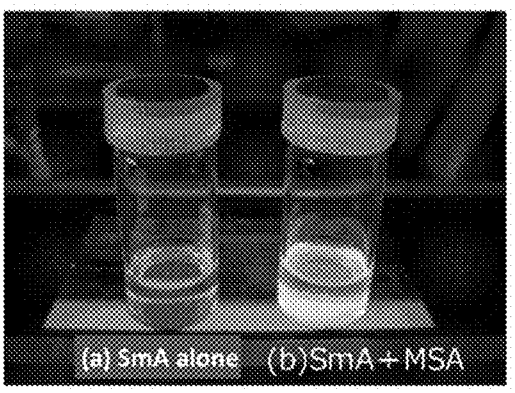
FIG. 7 shows a photograph for confirming fluorescence emission obtained in Example 5.

A SmA solution was prepared by dissolving 0.1 g of samarium (III) acetate hydrate (SmA) in 3 ml of dimethyl sulfoxide (DMSO). Next, 0.2 ml of an acetonitrile solution (0.1 mol/L) of MSA was added to 1.5 ml of the SmA solution to prepare an SmA solution containing MSA. The two resulting solutions were excited with a UV lamp (wavelength 365 nm) to confirm whether fluorescence emission was present (FIG. 7). As a result, it was found that the SmA alone solution (a) does not exhibit fluorescence emission, but the solution (b) with added MSA exhibits red fluorescence emission characteristic of the samarium complex, indicating that methyl salicylate can be sensed.

Comparative Example 3

Figure 8:
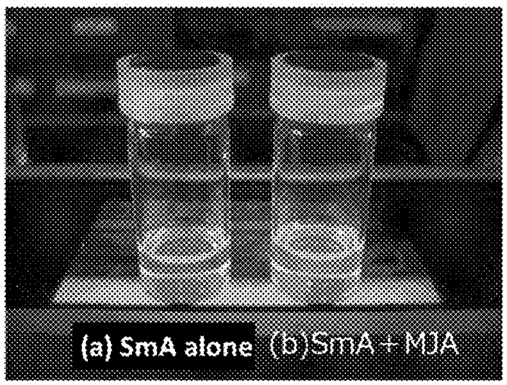
FIG. 8 shows a photograph for confirming fluorescence emission obtained in Comparative Example 3.

A SmA solution was prepared by dissolving 0.1 g of samarium (III) acetate hydrate (SmA) in 3 ml of DMSO. Next, 0.2 ml of an acetonitrile solution (0.1 mol/L) of methyl jasmonate (MJA) was added to 1.5 ml of the SmA solution to prepare an SmA solution containing MJA. The two resulting solutions were excited with a UV lamp (wavelength 365 nm) to confirm whether fluorescence emission was present (FIG. 8). As a result, it was found that neither the SmA alone solution (a) nor the solution (b) with added MJA exhibits fluorescence emission.

From the results of Example 5 and Comparative Example 3, it was found that SmA can selectively sense methyl salicylate, which is released by a plant at the time of pathogen infection.

Example 6

Figure 9:
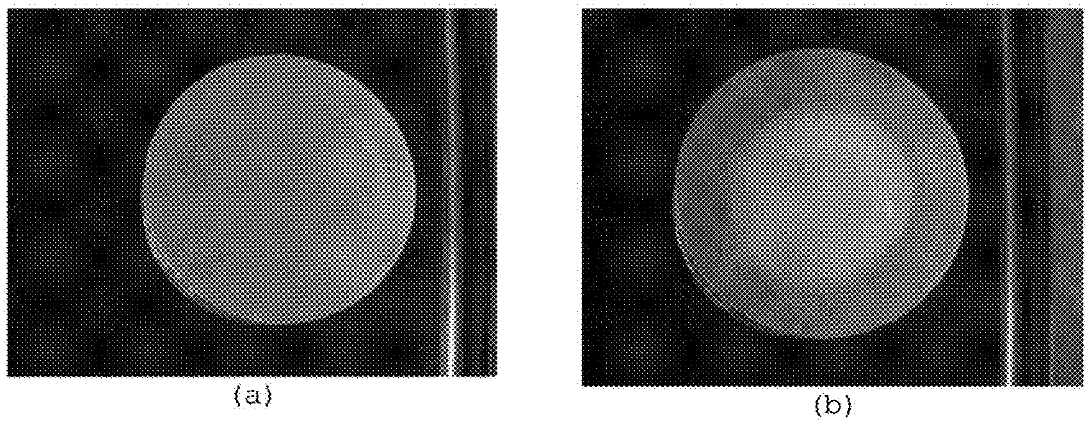
FIG. 9 shows photographs for confirming fluorescence emission obtained in Example 6.

0.2 ml of a solution obtained by dissolving 0.2 g of dysprosium (III) acetate tetrahydrate (DyA) in 2 ml of methanol was dropped on a circular filter paper (45 mmΦ) and dried to obtain a filter paper containing DyA. The obtained filter paper was excited with a UV lamp (wavelength 365 nm) to confirm whether fluorescence emission was present (FIG. 9(*a*)). Next, 0.03 ml of an acetonitrile solution (0.1 mol/L) of methyl salicylate (MSA), which is released when a plant is infected by a pathogen, was dropped on that filter paper and dried, and the obtained filter paper was similarly excited with a UV lamp to confirm whether fluorescence emission was present (FIG. 9(*b*)). As a result, it was found that DyA alone does not exhibit fluorescence, but DyA reacts with methyl salicylate and exhibits yellow fluorescence emission, indicating that methyl salicylate can be sensed.

Comparative Example 4

Figure 10:
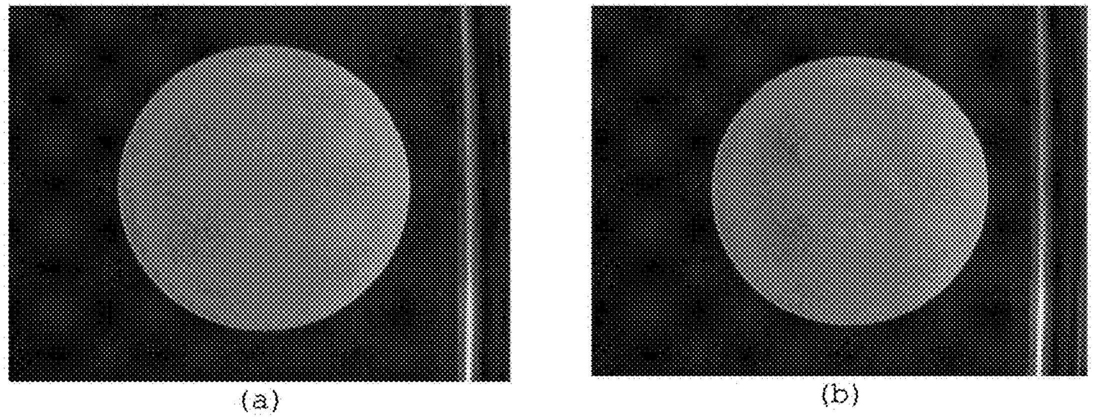
FIG. 10 shows photographs for confirming fluorescence emission obtained in Comparative Example 4.

0.2 ml of a solution obtained by dissolving 0.2 g of dysprosium (III) acetate tetrahydrate (DyA) in 2 ml of methanol was dropped on a circular filter paper (45 mmΦ) and dried to obtain a filter paper containing DyA. The obtained filter paper was excited with a UV lamp (wavelength 365 nm) to confirm whether fluorescence emission was present (FIG. 10(*a*)). Next, 0.03 ml of an acetonitrile solution (0.1 mol/L) of methyl jasmonate, which is a signal substance released when a plant undergoes damage by an insect pest, was dropped on that filter paper and dried, and the obtained filter paper was similarly excited with a UV lamp to confirm whether fluorescence emission was present (FIG. 10(*b*)). As a result, it was found that DyA does not react with methyl jasmonate and not exhibit fluorescence emission.

From the results of Example 6 and Comparative Example 4, it was found that DyA can selectively sense methyl salicylate, which is released by a plant at the time of pathogen infection.

Example 7

Figure 11:
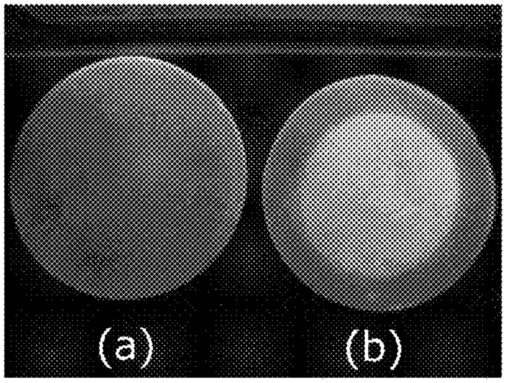
FIG. 11 shows a photograph for confirming the fluorescence emission obtained in Example 7.

0.2 ml of a solution obtained by dissolving 0.05 g of terbium (III) chloride hexahydrate (TbC) dissolved in 2 ml of water was dropped on a circular filter paper (45 mmΦ) and dried to obtain a filter paper containing TbC. The obtained filter paper was excited with a UV lamp (wavelength 365 nm) to confirm whether fluorescence emission was present (FIG. 11(*a*)). Next, 0.03 ml of an acetonitrile solution (0.1 mol/L) of methyl salicylate (MSA), which is released when a plant is infected by a pathogen, was dropped on that filter paper and dried, and the obtained filter paper was similarly excited with a UV lamp to confirm whether fluorescence emission was present (FIG. 11(*b*)). As a result, it was found that TbC alone does not exhibit fluorescence, but TbC reacts with methyl salicylate and exhibits fluorescence emission, indicating that methyl salicylate can be sensed.

Comparative Example 5

Figure 12:
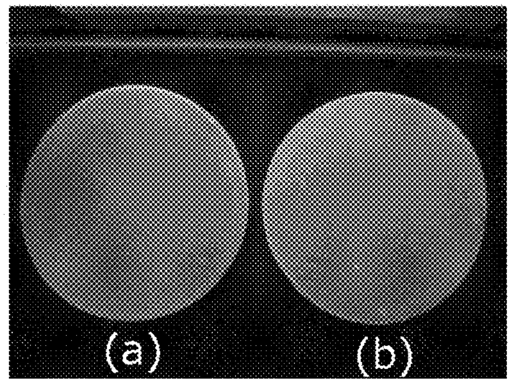
FIG. 12 shows a photograph for confirming fluorescence emission obtained in Comparative Example 5.

0.2 ml of a solution obtained by dissolving 0.05 g of terbium (III) chloride hexahydrate (TbC) in 2 ml of water was dropped on a circular filter paper (45 mmΦ) and dried to obtain a filter paper containing TbC. The obtained filter paper was excited with a UV lamp (wavelength 365 nm) to confirm whether fluorescence emission was present (FIG. 12(*a*)). Next, 0.03 ml of an acetonitrile solution (0.1 mol/L) of methyl jasmonate, which is a signal substance released when a plant undergoes damage by an insect pest, was dropped on that filter paper and dried, and the obtained filter paper was similarly excited with a UV lamp to confirm whether fluorescence emission was present (FIG. 12(*b*)). As a result, it was found that TbC does not react with methyl jasmonate and not exhibit fluorescence emission.

From the results of Example 7 and Comparative Example 5, it was found that TbC can selectively sense methyl salicylate, which is released by a plant at the time of pathogen infection.

Synthesis Example 1

[Complex of Terbium Acetate and Triphenylphosphine Oxide (TbA-TPO)]

0.3 g of terbium acetate tetrahydrate and 0.409 g of triphenylphosphine oxide are dissolved in 15 ml of methanol, and the resultant are heated to reflux for 4 hours. After cooling, the precipitated crystals were separated by filtration to obtain 0.177 g of the desired complex of terbium acetate and triphenylphosphine oxide.

Formula (4)

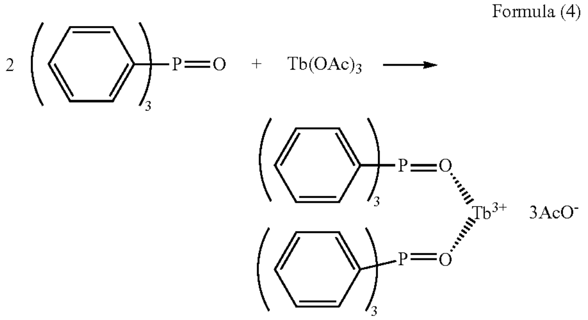

Synthesis Example 2

[Complex of Terbium Acetate and Tris(4-Methoxyphenyl) Phosphine Oxide (TbA-MTPO)]

0.3 g of terbium acetate tetrahydrate and 0.665 g of tris(4-methoxyphenyl) phosphine oxide were dissolved in 15 ml of methanol and the resultant are heated to reflux for 4 hours. After cooling, the precipitated crystals were separated by filtration to obtain 0.118 g of the desired complex of terbium acetate and tris(4-methoxyphenyl) phosphine oxide.

Formula (5)

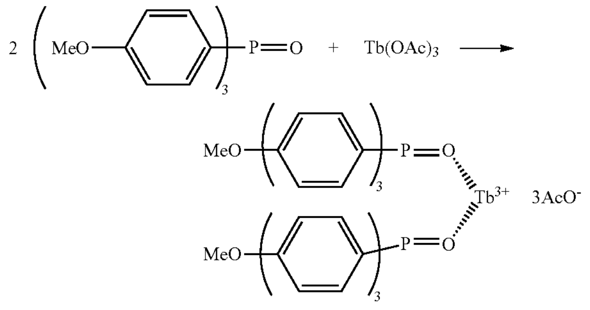

Example 8

0.2 ml of a solution obtained by dissolving 0.01 g of the complex (TbA-TPO) of terbium acetate and triphenylphosphine oxide in 1 ml of DMSO was dropped on a circular filter paper (45 mmΦ) and dried to obtain a filter paper containing TbA-TPO. The obtained filter paper was excited with a UV lamp (wavelength 365 nm) to confirm whether fluorescence emission was present (FIG. 13(*a*)). Next, an acetonitrile solution of methyl salicylate (MSA), which is released when a plant is infected by a pathogen, was dropped on that filter paper and dried, and the obtained filter paper was similarly excited with a UV lamp to confirm whether fluorescence emission was present (FIG. 13(*b*)). As a result, it was found that TbA-TPO alone does not exhibit fluorescence, but TbA-TPO reacts with methyl salicylate and exhibits fluorescence emission, indicating that methyl salicylate can be sensed.

Figure 13:
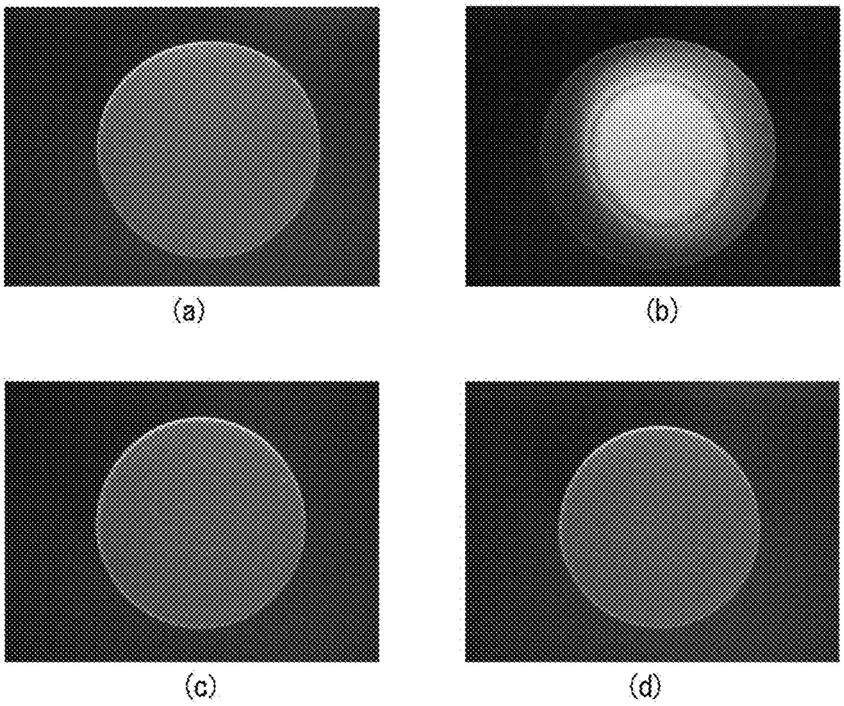
FIG. 13 shows photographs for confirming fluorescence emission obtained in Example 8.

On the filter paper containing TbA-TPO (FIG. 13(*c*)), an acetonitrile solution of methyl jasmonate (MJA), which is a signal substance released when a plant undergoes damage by an insect pest, was dropped and dried. The obtained filter paper was similarly excited with a UV lamp to confirm whether fluorescence emission was present (FIG. 13(*d*)). As a result, it was found that TbA-TPO does not react with methyl jasmonate and does not exhibit fluorescence emission, indicating that TbA-TPO can selectively sense methyl salicylate, which is released by a plant at the time of pathogen infection.

Example 9

0.2 ml of a solution obtained by dissolving 0.01 g of the complex (TbA-MTPO) of terbium acetate and tris(4-methoxytriphenyl) phosphine oxide in 1 ml of DMSO was dropped on a circular filter paper (45 mmΦ) and dried to obtain a filter paper containing TbA-MTPO. The obtained filter paper was excited with a UV lamp (wavelength 365 nm) to confirm whether fluorescence emission was present (FIG. 14(*a*)). Next, an acetonitrile solution of methyl salicylate (MSA), which is released when a plant is infected by a pathogen, was dropped on that filter paper and dried, and the obtained filter paper was similarly excited with a UV lamp to confirm whether fluorescence emission was present (FIG. 14(*b*)). As a result, it was found that TbA-MTPO alone does not exhibit fluorescence, but TbA-MTPO reacts with methyl salicylate and exhibits fluorescence emission, indicating that methyl salicylate can be sensed.

Figure 14:
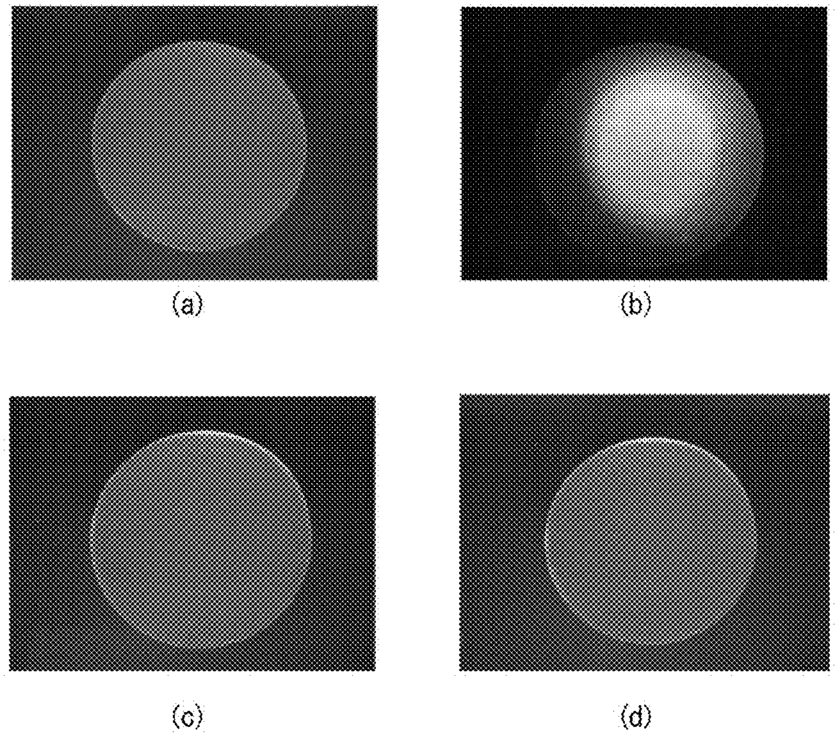
FIG. 14 shows photographs for confirming fluorescence emission obtained in Example 9.

On the filter paper containing TbA-MTPO (FIG. 14(*c*)), an acetonitrile solution of methyl jasmonate (MJA), which is a signal substance released when a plant undergoes damage by an insect pest, was dropped and dried. The obtained filter paper was similarly excited with a UV lamp to confirm whether fluorescence emission was present (FIG. 14(*d*)). As a result, it was found that TbA-MTPO does not react with methyl jasmonate and does not exhibit fluorescence emission, indicating that TbA-MTPO can selectively sense methyl salicylate, which is released by a plant at the time of pathogen infection.

Example 10

[Fluorescence Spectrometry]

Figure 15:
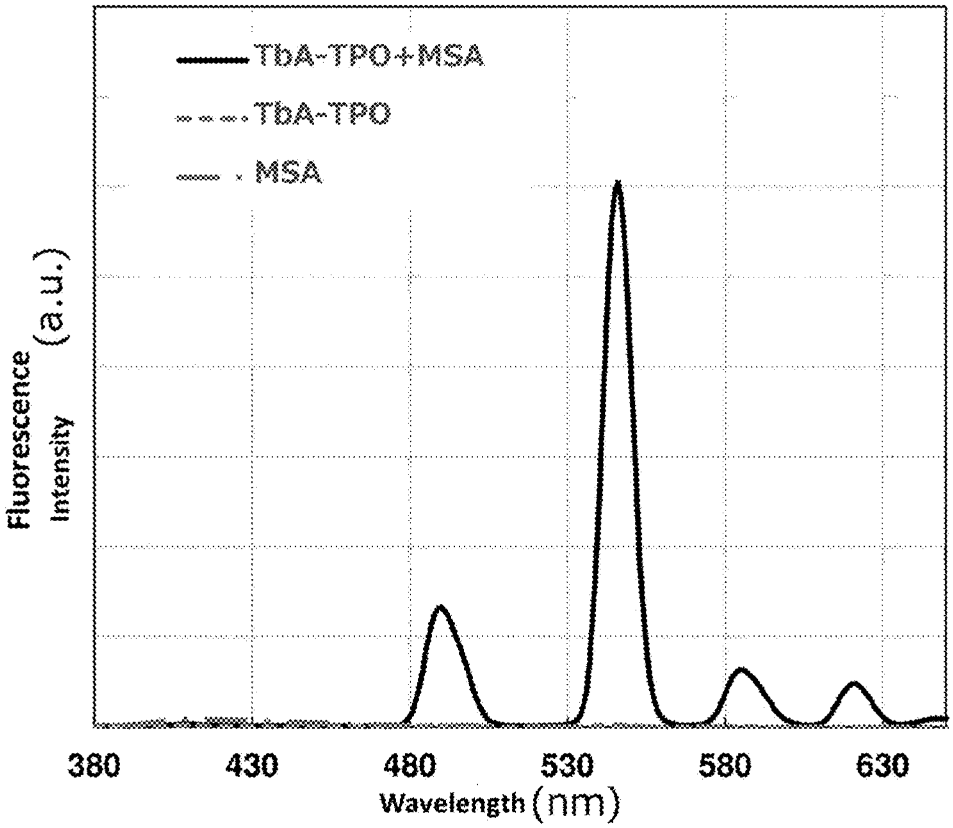
FIG. 15 shows a fluorescence spectrum curve obtained in Example 10.

0.9 ml of a DMSO solution of the complex (TbA-TPO) of terbium acetate tetrahydrate (TbA) and triphenylphosphine oxide (concentration: 0.0015 mol/L) was mixed with 0.1 ml of a DMSO solution of methyl salicylate (MSA) (concentration: 0.0015 mol/L), and after 10 minutes, the mixed solution was diluted by 20 times. Thereafter, the resulting solution was put in a quartz cell and the fluorescence spectrum was measured at an excitation wavelength of 365 nm. Also, 0.9 ml of DMSO solution of TbA-TPO (concentration 0.0015 mol/L) and 0.1 ml of DMSO were mixed, the mixed solution was further diluted by 20 times, the resulting solution was put in a quartz cell, and the fluorescence spectrum was measured at an excitation wavelength of 365 nm. Similarly, 0.1 ml of DMSO solution of MSA (concentration: 0.0015 mol/L) was mixed with 0.9 ml of DMSO, the mixed solution was further diluted by 20 times, and the resulting solution was put in a quartz cell, and the fluorescence spectrum was measured at an excitation wavelength of 365 nm. FIG. 15 shows the fluorescence spectrum curves obtained. The solid line represents the fluorescence spectrum of TbA-TPO+MSA, the dashed line represents the fluorescence spectrum of TbA-TPO alone, and the dash-dot-dash line represents the fluorescence spectrum of MSA alone.

These results revealed that TbA-TPO itself does not exhibit fluorescence, but TbA-TPO through reaction with MSA exhibits fluorescence emission (maximum wavelength of 546 nm). Further, it was found that MSA alone does not exhibit fluorescence emission in the range of 480 to 630 nm, but TbA-TPO reacts with methyl salicylate and exhibits fluorescence emission.

Example 11

[Detection of MSA on an Agarose Gel Containing a Rare Earth Salt]

Figure 16:
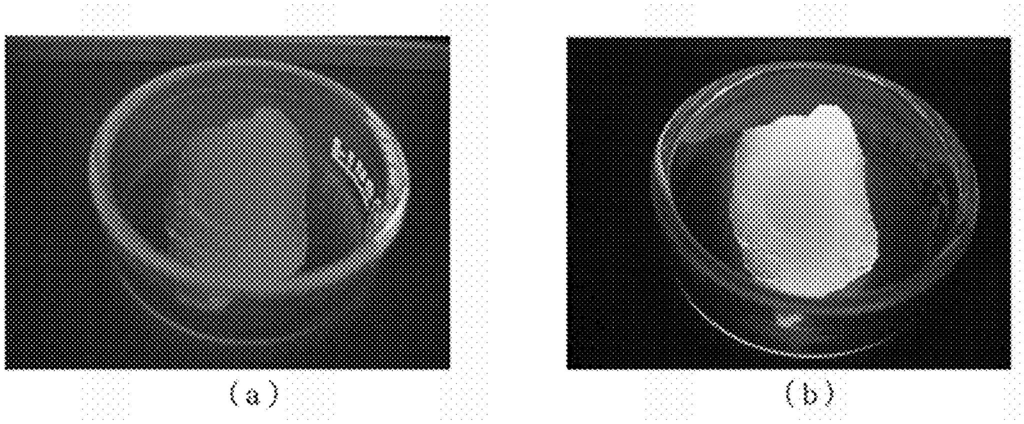
FIG. 16 shows photographs confirming for fluorescence emission obtained in Example 11.
Figure 1:
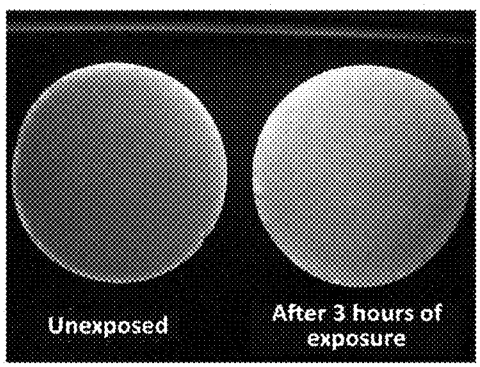

0.125 g of terbium acetate tetrahydrate (TbA) and 1 g of agarose were dispersed in 49 g of water, and the agarose was dissolved and solated by heating and stirring at 95° C. Then, the resultant was allowed to cool to obtain a gel containing TbA. A portion of the resulting gel was taken out and excited with a UV lamp (wavelength 365 nm) to confirm whether fluorescence emission was present, and it was found that no fluorescence was observed (FIG. 16(*a*)).

Next, this gel and 10 mg of methyl salicylate placed in a Petri dish were left at rest and stored in a desiccator so that they are not in direct contact. After 6 hours, the gel was taken out, and the gel was excited with a UV lamp (wavelength 365 nm) to evaluate whether fluorescence emission was present, which confirmed yellow-green fluorescence (FIG. 16(*b*)). From this result, it was found that TbA-containing gel can sense methyl salicylate, which is released by a plant at the time of pathogen infection as a volatile signal.

Example 12

[Detection of MSA at a Concentration of 13 ppm].

0.2 ml of a solution obtained by dissolving 0.1 g of terbium acetate tetrahydrate (TbA) in 2 ml of water was dropped on a circular filter paper (45 mm D) and dried to obtain a filter paper containing TbA. The obtained filter paper was placed in an 800 ml capacity desiccator adjusted to a MSA concentration of 13 ppm, and after 3 hours, the filter paper was taken out and confirmed whether fluorescence emission was present at an excitation wavelength of 365 nm. The results are shown in FIG. 17. In the unexposed condition (left), the yellow-green fluorescent emission characteristic of the Tb complex was not observed, but after 3 hours of exposure (right), the yellow-green fluorescent emission was confirmed. From this result, it was found that TbA can sense MSA at the 10 ppm level.

Example 13

[Quantitative Evaluation of Fluorescence Intensity]

Figure 18:
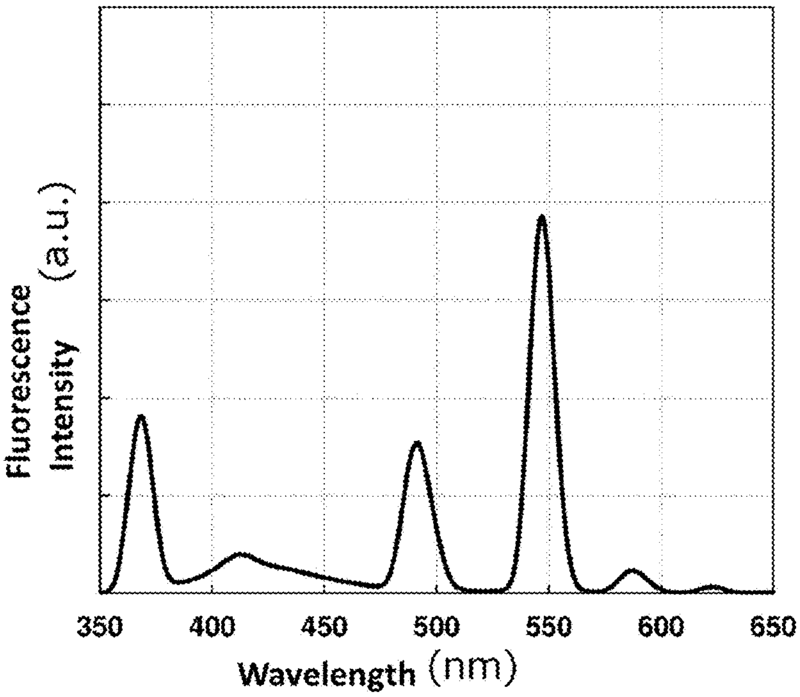
FIG. 18 shows a fluorescence spectrum curve in Example 13.

0.5 ml of DMSO solution of TbA (concentration: 0.0005 mol/L) and 0.5 ml of DMSO solution of MSA (concentration: 0.0005 mol/L) were added, after 10 minutes, the mixed solution was diluted by 40 times and the resulting solution was put in a quartz cell and the fluorescence spectrum was measured at excitation wavelength of 365 nm. Consequently, FIG. 18 shows the fluorescence spectrum curve obtained. The peak wavelength at which the fluorescence intensity was strongest was 547 nm, indicating that the fluorescence emission wavelength was characteristic to the terbium complex. Next, 0.9 ml of DMSO solution of TbA (concentration: 0.0005 mol/L) and 0.1 ml of DMSO solution of MSA (concentration: 0.0005 mol/L) were added, after 10 minutes, the mixed solution was diluted by 40 times, the fluorescence spectrum was measured at an excitation wavelength of 365 nm and the fluorescence intensity at the wavelength of 547 nm was determined.

Figure 19:
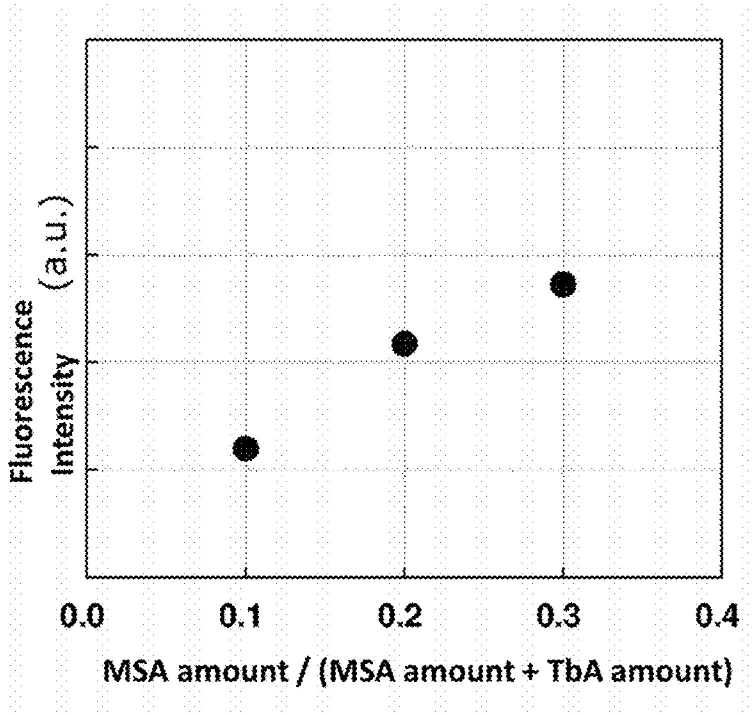
FIG. 19 shows a graph plotting a fluorescence intensity obtained in Example 13.

In the same manner, the fluorescence intensity with 0.8 ml of the TbA solution and 0.2 ml of the MSA solution, and also the fluorescence intensity with 0.7 ml of the TbA solution and 0.3 ml of the MSA solution were determined. The obtained fluorescence intensities are plotted in FIG. 19. From the results, it was found that, as the ratio of MSA is increased, the fluorescence intensity is also increased, indicating that MSA can be quantitatively detected.

Example 14

[Measurement of Electrochemical Behavior]

An electrolyte solution was prepared by dissolving tetrabutylammonium perchlorate as a supporting electrolyte in DMSO (concentration: 0.1 mol/L), 10 ml of the electrolyte solution was placed in a glass container, and an electrochemical cell having three electrodes, comprising a working electrode, a counter electrode, and a reference electrode, was constituted. Note that glassy carbon was used as the working electrode, Pt as the counter electrode, and $Ag/Ag^+$ electrode as the reference electrode. To this, 0.1 ml of a solution of TbA in DMSO (concentration: 0.1 mol/L) was added, and the cyclic voltammetry (CV) was measured at room temperature (sweep potential: −0.8 to 1.2 V, sweep rate: 0.1 V/s).

Next, 0.1 ml of DMSO solution (concentration: 0.1 mol/L) of methyl salicylate (MSA) was added to it, and the CV measurement was carried out in the same manner.

Figure 20:
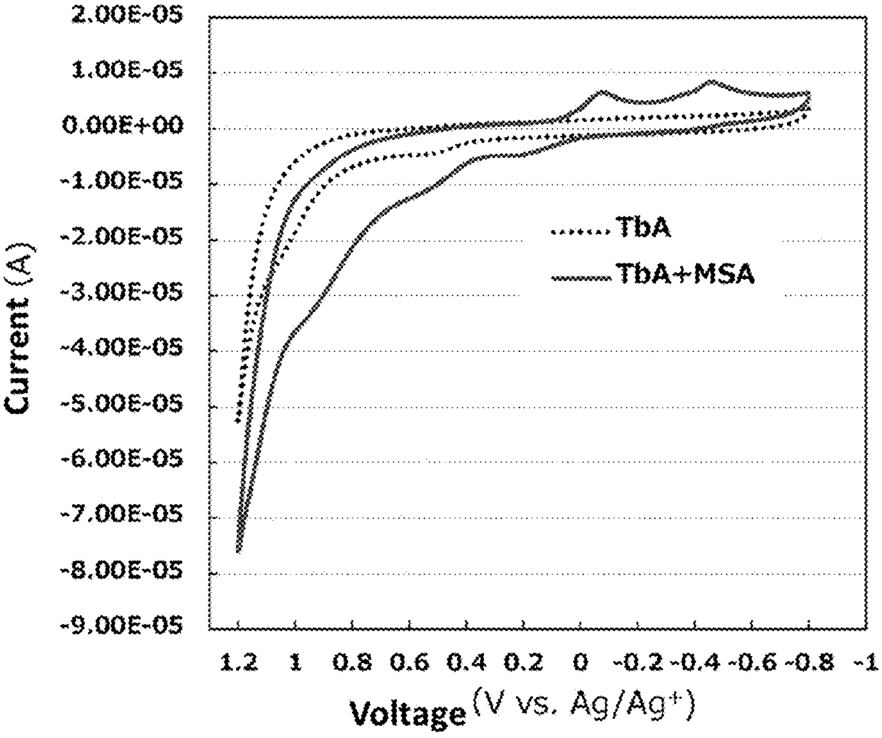
FIG. 20 shows a graph showing a current-voltage curve (cyclic voltammogram) obtained in Example 14.

The obtained current-voltage curve (cyclic voltammogram) is shown in FIG. 20. The dashed line shows the measurement result of TbA alone, and the solid line shows the result after adding MSA to TbA. The results show that after the addition of MSA, new reduction peaks appear at potentials of −0.08 V and −0.46 V as compared to that before the addition. This indicates that methyl salicylate, a plant hormone, can be sensed through a change in current value, for example, by monitoring the current value flowing through the electrode at a voltage (−0.08 V and −0.46 V for $Ag/Ag^+$ electrode) where the current value is greatly changed before and after the reaction with MSA.

Synthesis Example 3

[Terbium Pivalate]

1 g of terbium chloride hexahydrate was dissolved in 20 ml of water, to which was added 1.142 g of sodium pivalate dissolved in 20 ml of water, and stirred at room temperature for 1 hour. The precipitated crystals were separated by filtration and washed with water to obtain 0.742 g of white powdered terbium pivalate.

Example 15

[Fluorescence Detection of Methyl Salicylate by Terbium Pivalate].

Figure 21:
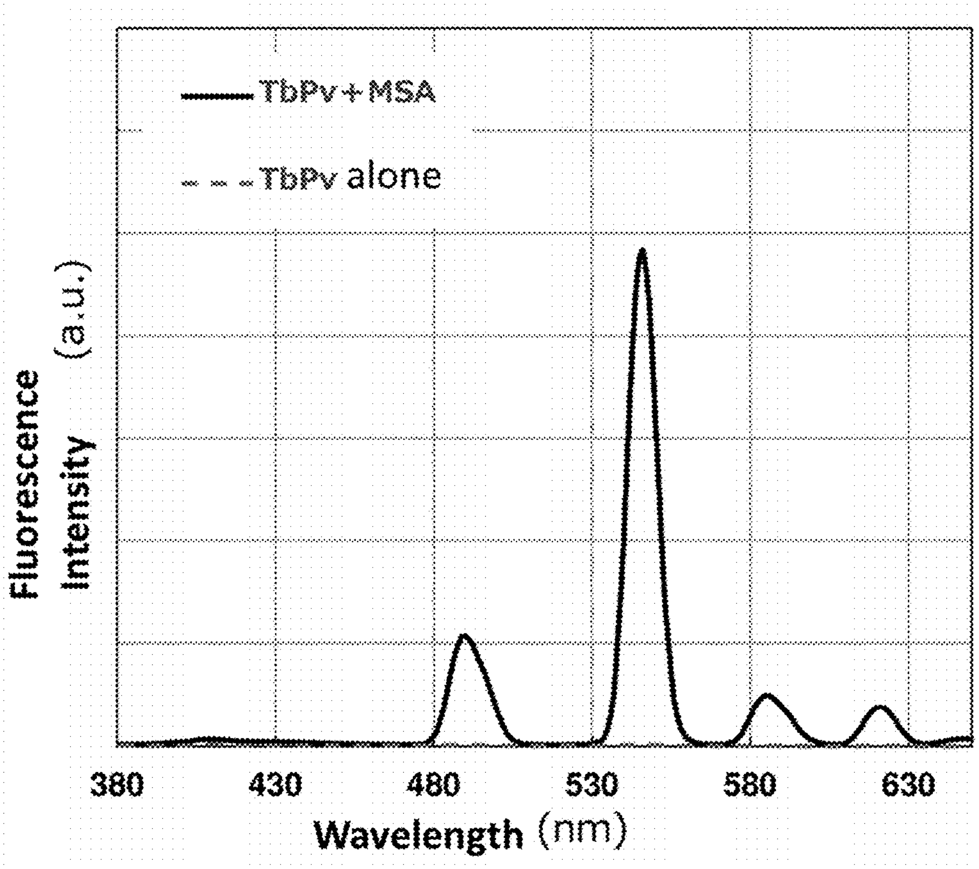
FIG. 21 shows a fluorescence spectrum curve obtained in Example 15.

0.9 ml of a DMSO solution of terbium pivalate (TbPv) in DMSO (concentration: 0.0015 mol/L) and 0.1 ml of a DMSO solution of methyl salicylate (MSA) (concentration: 0.0015 mol/L) were mixed, after 10 minutes, the mixture was diluted by 20 times. Thereafter, the resulting solution was put in a quartz cell and the fluorescence spectrum was measured at an excitation wavelength of 365 nm. Also, 0.9 ml of a DMSO solution of TbPv (concentration: 0.0015 mol/L) was mixed with 0.1 ml of DMSO, the mixture was further diluted by 20 times, and the solution was put in a quartz cell, and the fluorescence spectrum was measured at an excitation wavelength of 365 nm. FIG. 21 shows the obtained fluorescence spectrum curve. The solid line represents the fluorescence spectrum of TbPv+MSA, and the dashed line represents the fluorescence spectrum of TbPv alone. From these results, it was found that TbPv itself does not exhibit fluorescence, but reacts with MSA and exhibits fluorescence emission (maximum wavelength of 546 nm).

The whole or part of the example embodiments disclosed above may be described as, but not limited to, the following supplementary notes.

(Supplementary Note 1)

A sensing method for sensing methyl salicylate, using a rare earth compound as a receptor that selectively recognizes methyl salicylate.

(Supplementary Note 2)

The sensing method according to Supplementary note 1, wherein the rare earth compound is acetate, chloride, oxalate, nitrate, propionate, isobutyrate, or pivalate of:

scandium (Sc), yttrium (Y), lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), or lutetium (Lu).

(Supplementary Note 3)

The sensing method according to Supplementary note 1, wherein the rare earth compound is acetate, chloride, oxalate, nitrate, propionate, isobutyrate, or pivalate of:

samarium (Sm), europium (Eu), gadolinium (Gd), terbium (Tb), or dysprosium (Dy).

(Supplementary Note 4)

The sensing method according to Supplementary note 1, wherein the rare earth compound is a complex compound formed with a phosphine oxide derivative.

(Supplementary Note 5)

The sensing method according to any one of Supplementary notes 1 to 4, wherein the sensing utilizes a phenomenon in which methyl salicylate reacts with the rare earth compound to form a rare earth complex and exhibit fluorescence emission.

(Supplementary Note 6)

The sensing method according to any one of Supplementary notes 1 to 5, wherein the sensing utilizes a phenomenon in which electrochemical behavior is changed by a reaction of the rare earth compound and methyl salicylate.

(Supplementary Note 7)

The sensing method according to Supplementary note 6, wherein the sensing utilizes a change in current value caused by a reaction of the rare earth compound and methyl salicylate.

(Supplementary Note 8)

A methyl salicylate sensor for detecting methyl salicylate, at least comprising:

i) a recognition section for methyl salicylate that comprises a rare earth compound; and ii) a detection section that detects recognition of methyl salicylate by the recognition section.

(Supplementary Note 9)

A method for detecting pathogen infection in a crop, comprising installing the methyl salicylate sensor according to Supplementary note 8 in a vicinity of the crop, and detecting methyl salicylate by the sensor.

(Supplementary Note 10)

A methyl salicylate sensor for detecting methyl salicylate, at least comprising: a recognition section for methyl salicylate that comprises a rare earth compound, which is a receptor that selectively recognizes methyl salicylate; and a detection section that detects recognition of methyl salicylate by the recognition section, the detection section comprising an optical and/or electrochemical detection element and a computer, wherein the methyl salicylate sensor has a program that causes the computer to execute:

i) a step of receiving a signal from the optical and/or electrochemical detection element;
ii) a step of analyzing the received signal to determine presence or absence of methyl salicylate and/or a concentration thereof; and
iii) a step of outputting an analysis result.

(Supplementary Note 11)

A program controlling a methyl salicylate sensor for detecting methyl salicylate, the methyl salicylate sensor at least comprising: a recognition section for methyl salicylate that comprises a rare earth compound, which is a receptor that selectively recognizes methyl salicylate; and a detection section that detects recognition of methyl salicylate by the recognition section, the detection section comprising an optical and/or electrochemical detection element and a computer, wherein the program causes the computer to execute:

i) a step of receiving a signal from the optical and/or electrochemical detection element;
ii) a step of analyzing the received signal to determine presence or absence of methyl salicylate and/or a concentration thereof; and
iii) a step of outputting an analysis result.

(Supplementary Note 12)

A detection method for detecting methyl salicylate, comprising: (i) a step of allowing a rare earth compound to react with methyl salicylate to form a complex; (ii) a step of exposing the complex to excitation light; and (iii) a step of detecting fluorescence emitted by the complex.

(Supplementary Note 13)

The detection method according to Supplementary note 12, wherein a wavelength in a range of 200 to 400 nm is used as the excitation wavelength.

(Supplementary Note 14)

The detection method according to Supplementary note 12 or 13, further comprising a step of comparing an intensity of the detected fluorescence with a predetermined reference value to determine a concentration of methyl salicylate.

Supplementary Note 15)

A detection method for detecting methyl salicylate, comprising: (i) a step of allowing a rare earth compound to react with methyl salicylate in a solution to form a complex; (ii) a step of measuring a current flowing through the solution under a certain voltage; and (iii) a step of detecting a change in current value caused by formation of the complex.

(Supplementary Note 16)

The detection method according to Supplementary note 15, wherein a value of the voltage is in a range of −1 to 2 V.

(Supplementary Note 17)

The detection method according to Supplementary note 15 or 16, wherein the solution comprises tetrabutylammonium perchlorate as a supporting electrolyte.

(Supplementary Note 18)

The detection method according to any one of Supplementary notes 15 to 17, further comprising a step of comparing the detected change in current value with a predetermined reference value to determine a concentration of methyl salicylate.

(Supplementary Note 19)

The detection method according to any one of Supplementary notes 12 to 18, wherein the rare earth compound is selected from the group consisting of terbium (III) acetate tetrahydrate, gadolinium (III) acetate tetrahydrate, samarium (III) acetate hydrate, dysprosium (III) acetate tetrahydrate, terbium pivalate and terbium (III) chloride hexahydrate.

(Supplementary Note 20)

A methyl salicylate sensor for detecting methyl salicylate, at least comprising: (i) a recognition section for methyl salicylate that comprises a rare earth compound; and (ii) a detection section that optically detects recognition of methyl salicylate by the recognition section.

(Supplementary Note 21)

The methyl salicylate sensor according to Supplementary note 20, wherein the optical detection section at least comprises an excitation light source and a detection element.

(Supplementary Note 22)

A methyl salicylate sensor for detecting methyl salicylate, at least comprising: (i) a recognition section for methyl salicylate that comprises a rare earth compound; and (ii) a detection section that electrochemically detects recognition of methyl salicylate by the recognition section.

(Supplementary Note 23)

The methyl salicylate sensor according to Supplementary note 22, wherein the electrochemical detection section comprises an electrochemical cell having an electrode that detects a current caused by oxidation of a complex formed by the rare earth compound and methyl salicylate.

(Supplementary Note 24)

A method for detecting pathogen infection in a crop, comprising installing the methyl salicylate sensor according to Supplementary note 10 in a vicinity of the crop, and detecting methyl salicylate by the sensor.

(Supplementary Note 25)

The method for detecting pathogen infection in a crop according to Supplementary note 9 or 24, wherein the methyl salicylate sensor according to Supplementary note 10 is installed within 2 m from the crop.

While the invention has been described with reference to example embodiments and examples thereof, the invention is not limited to these embodiments and examples. Various changes that can be understood by those of ordinary skill in the art may be made to forms and details of the present invention without departing from the spirit and scope of the present invention.

INDUSTRIAL APPLICABILITY

The sensing according to embodiments of the present invention in which a rare earth compound is used as a receptor for detecting methyl salicylate, which is a plant hormone, selectively forms a complex with methyl salicylate and also develops a fluorescence emission phenomenon and a change in electrochemical behavior, and thus enables selective detection of methyl salicylate, which is a plant hormone released when a plant is infected by a pathogen.

By using a sensor in which the rare earth compound serves as the recognition section, disease infection in a plant can be detected at an early stage, and specifically, as a sensor that can detect disease infection of a crop at an early stage, it can be used as a novel sensor for agricultural ICT in greenhouses and other horticultural facilities.

The invention claimed is:

1. A sensing method for sensing methyl salicylate, using a rare earth compound as a receptor that recognizes methyl salicylate.

2. The sensing method according to claim 1, wherein the rare earth compound is acetate, chloride, oxalate, nitrate, propionate, isobutyrate, or pivalate of:

scandium (Sc), yttrium (Y), lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), or lutetium (Lu).

3. The sensing method according to claim 1, wherein the rare earth compound is acetate, chloride, oxalate, nitrate, propionate, isobutyrate, or pivalate of:

samarium (Sm), europium (Eu), gadolinium (Gd), terbium (Tb), or dysprosium (Dy).

4. The sensing method according to claim 1, wherein the rare earth compound is a complex compound formed with a phosphine oxide derivative.

5. The sensing method according to claim 1, wherein the sensing utilizes a phenomenon in which methyl salicylate reacts with the rare earth compound to form a rare earth complex and exhibit fluorescence emission.

6. The sensing method according to claim 1, wherein the sensing utilizes a phenomenon in which electrochemical behavior is changed by a reaction of the rare earth compound and methyl salicylate.

7. The sensing method according to claim 6, wherein the sensing utilizes a change in current value caused by a reaction of the rare earth compound and methyl salicylate.

8. A methyl salicylate sensor for detecting methyl salicylate, at least comprising:

i) a recognition section for methyl salicylate that comprises a rare earth compound; and ii) a detection section that detects recognition of methyl salicylate by the recognition section.

9. A method for detecting pathogen infection in a crop, comprising installing the methyl salicylate sensor according to claim 8 in a vicinity of the crop, and detecting methyl salicylate by the sensor.

10. The methyl salicylate sensor for detecting methyl salicylate according to claim 8, the detection section comprising an optical and/or electrochemical detection element and a computer, wherein the methyl salicylate sensor has a program that causes the computer to execute:

i) receiving a signal from the optical and/or electrochemical detection element;

ii) analyzing the received signal to determine presence or absence of methyl salicylate and/or a concentration thereof; and iii) outputting an analysis result.

11. The methyl salicylate sensor for detecting methyl salicylate according to claim 8, the detection section comprises an optical detection section that optically detects recognition of methyl salicylate by the recognition section.

12. The methyl salicylate sensor according to claim 11, wherein the optical detection section at least comprises an excitation light source and a detection element.

13. The methyl salicylate sensor for detecting methyl salicylate according to claim 8, the detection section comprises an electrochemical detection section that electrochemically detects recognition of methyl salicylate by the recognition section.

14. The methyl salicylate sensor according to claim 13, wherein the electrochemical detection section comprises an electrochemical cell having an electrode that detects a current caused by oxidation of a complex formed by the rare earth compound and methyl salicylate.

15. A method for detecting pathogen infection in a crop, comprising installing the methyl salicylate sensor according to claim 10 in a vicinity of the crop, and detecting methyl salicylate by the sensor.

16. The method for detecting pathogen infection in a crop according to claim 15, wherein the methyl salicylate sensor is installed within 2 m from the crop.

* * * * *